United States Patent [19]

Bassett

[11] Patent Number: 5,711,953

[45] Date of Patent: Jan. 27, 1998

[54] INSECT REPELLANT

[76] Inventor: John M. Bassett, 5490 13 Mile Rd., Rockford, Mich. 49341

[21] Appl. No.: 703,384

[22] Filed: Aug. 26, 1996

[51] Int. Cl.$^6$ .................................................. A01N 25/02
[52] U.S. Cl. .......................... 424/405; 424/406; 424/407; 424/195.1; 514/919
[58] Field of Search .................... 424/403, 405–407, 424/195.1; 514/919

[56] References Cited

U.S. PATENT DOCUMENTS

| | | | |
|---|---|---|---|
| 186,260 | 1/1877 | Margarit | 424/134 |
| 312,270 | 1/1885 | Hoag | 424/195.1 |
| 436,848 | 9/1890 | Farwell et al. | 424/195.1 |
| 1,871,949 | 8/1932 | Bottrell | 424/195.1 |
| 2,159,953 | 5/1939 | Proetto | 167/24 |
| 3,122,473 | 2/1964 | White et al. | 167/22 |
| 3,624,204 | 11/1971 | Stepanov et al. | 424/244 |
| 4,360,987 | 11/1982 | Lowder | 43/132 |
| 4,455,304 | 6/1984 | Yaralian | 424/195.1 |
| 4,518,593 | 5/1985 | Juvin et al. | 424/195.1 |
| 4,820,517 | 4/1989 | Pfeiffer et al. | 424/195.1 |
| 4,876,090 | 10/1989 | Weisler | 424/195.1 |
| 5,166,177 | 11/1992 | Thomas et al. | 374/557 |
| 5,368,866 | 11/1994 | Loucas | 424/581 |
| 5,419,077 | 5/1995 | Tombarelli | 43/557 |
| 5,429,817 | 7/1995 | McKenzie | 424/195.1 |
| 5,453,274 | 9/1995 | Green | 424/403 |
| 5,456,916 | 10/1995 | Kurata et al. | 424/408 |
| 5,466,459 | 11/1995 | Wilson | 424/407 |

OTHER PUBLICATIONS

Foster The Organic Gardener Vintage Books, N.Y. 1972 pp. 59, 121, 122, 163.
Terlingaa—Label.

*Primary Examiner*—Neil S. Levy
*Attorney, Agent, or Firm*—Price, Heneveld, Cooper, DeWitt and Litton

[57] ABSTRACT

An insect repellant of biodegradable ingredients, primarily food products or foodstuff derivatives, that is safe and effective over long periods on animals and humans, wherein the insect repellant comprises two basic ingredients which are small amounts of a garlic extract component and a hot pepper extract component in a surfactant and carrier solution, preferably employing vinegar. It requires no petroleum-based materials. A method for repelling insects is also described.

17 Claims, No Drawings

INSECT REPELLANT

BACKGROUND OF THE INVENTION

This invention relates to insect repellants, and particularly to composition which are effective as insect repellants when applied to animals, such as horses, herd animals, dogs, and cats and when applied to humans.

The inventor herein, a veteran horseman, has shared with others in animal husbandry the known, common experience of biting insect attacks on animals. Horses are particularly troubled by such aggressive species as those commonly called "deer flies," as well as other types of flies and biting insects. Aside from the pain and discomfort to the animals caused by these creatures, there is also the potential for resulting infections, transfer of diseases, loss of weight due to inability to rest properly, and even death of the animal. These facts are well known by anyone involved in animal husbandry. In addition to the fact that humans are also prone to direct attack by biting insects, the problems presented to animals become a problem to humans, e.g., when riding horses, since the animal can become unmanageable, resulting in potential injury of horse and/or rider, or can respond to insect irritation in ways that further attract insects, which then pester the rider as well.

Many and various compositions have been marketed for application as by rubbing or spraying on the animal, in order to repel insects. Some of these are considered somewhat effective for a short time period, but require frequent liberal application. Moreover, available products typically have a petroleum base which knowledgeable people are reluctant to apply liberally to the hair, fur, and skin of animals.

The prior art describes various compositions containing natural substances such as garlic, hot pepper, or vinegar which have been used in trying to combat attack by insects and other animals. For example, garlic juice, hot pepper, acetic acid, or vinegar have been used separately or in various combinations to apply to plants, ant paths, and bee hives to repel deer, birds, bees, ants, and herbivorous insects. U.S. Pat. No. 3,122,473 to White et al. (acetic acid to temporarily repel bees from honeycombs); U.S. Pat. No. 4,455,304 to Yaralian (hot pepper and garlic composition applied to plants and soil to repel birds); U.S. Pat. No. 5,368,866 to Loucas (hot pepper, garlic, and vinegar composition applied to plants to repel deer); U.S. Pat. No. 5,429,817 to McKenzie (garlic juice applied to plants to repel herbivorous insects); U.S. Pat. No. 5,453,274 to Green (hot pepper-treated paper to repel ants, walking insects). In addition, U.S. Pat. No. 4,876,090 to Weisler describes the use of metabolites of ingested garlic oil, which seep through the animal's skin to repel fleas and ticks. And these three ingredients have been used separately in insecticide compositions for killing herbivorous insects, ants, earwigs, and lice. U.S. Pat. No. 186,260 to Margarit (garlic-containing composition applied to insects on plants); U.S. Pat. No. 312,270 to Hoag (hot pepper-containing composition applied to insects on plants); U.S. Pat. No. 4,518,593 to Juvin et al. (vinegar-containing louse shampoo); U.S. Pat. No. 5,419,077 to Tombarelli (vinegar-containing insecticide spray for direct application to insects generally).

However, no such composition has been found for application to skin, hair, fur, or garments to provide effective, long-term biting insect repellant activity to the wearer, that is also biodegradable and safe in extensive, liberal, and repeated use.

SUMMARY OF THE INVENTION

An object of this invention is to provide a novel insect repellant composed primarily of biodegradable ingredients, most of which are ordinarily food products or derivatives, and which is characterized by effectiveness over an extended time period and safety in extensive, liberal, and repeated use. The repellant requires no petroleum-based materials. Although liberal application of the repellant is not required for effectiveness, it can be liberally applied without concern. Tests have shown it to be highly effective, even for aggressive, biting insects such as deer flies, relieving animals and humans of the agony of many biting insects.

The unique insect repellant is composed primarily of ingredients which normally serve as human food items. There are four main components, namely a carrier, such as vinegar, and small amounts of a garlic extract component and a hot pepper extract component, as well as a surfactant component. The garlic extract and hot pepper extract component are mixed with the other two components while in a liquid form for ease of preparation of the repellant.

Preferably, the garlic extract component is in the form of garlic juice present in an amount of about 1 to 3% by volume, the hot pepper extract component is in the form a hot pepper sauce present in an amount of about 1 to 3% by volume, the surfactant component is in the form of a nonionic surfactant liquid mixture present in an amount of at least about 2% by volume, and the remainder is a carrier in the form of a vinegar.

DETAILED DESCRIPTION AND PREFERRED EMBODIMENT

The novel insect repellant employs four ingredients, three of which are in small but effective amounts, and the fourth being an appropriate carrier.

The ingredient in largest amount is the carrier. The carrier is liquid or substantially liquid in character. It is contemplated that the liquid carrier be water or an aqueous solution of a weak acid, preferably an aqueous solution of a saturated or unsaturated carboxylic, dicarboxylic, or tricarboxylic acid, or a derivative thereof, or mixture thereof, more preferably an aqueous solution of acetic acid or a derivative or mixture thereof, even more preferably a vinegar or a derivative or mixture thereof, and most preferably a wine or cider vinegar or a derivative or mixture thereof. Vinegar is a sour, aqueous liquid, generally containing about 4% to 8% acetic acid, obtained by the acetic fermentation of dilute, aqueous alcohol solutions, e.g., by bacterial fermentation of wine, apple cider, fruit juice, or dilute, distilled ethanol, or by mold fermentation of barley malt or beer. The carrier constitutes about 90 to 95% by volume of the composition, preferably about 91 to 94%. In addition to comprising the bulk of the composition, the carrier serves as a preservative for the insect repellant. In a preferred embodiment, the carrier is a natural, cider vinegar.

The second ingredient is a garlic extract component. The garlic extract component is a purified or unpurified: 1) extract of or preparation of *Allium spp., Armoracia spp., Brassica spp., Nasturtium spp.,* or *Raphanus spp.,* preferably a garlic, more preferably *Allium sativum,* or of a variety thereof, or a derivative thereof, or mixture thereof; or 2) preparation of or composition comprising a synthetic alkyl or alkenyl sulfide, disulfide, sulfinate, sulfenic acid, thiol, thiosulfinate, thiourea, or isothiocyanate, or a derivative thereof, or mixture thereof, preferably mono- or di-allyl, -methyl allyl, or -allyl propyl sulfide, disulfide, sulfinate, sulfenic acid, thiol, thiosulfinate, thiourea, or isothiocyanate, or a derivative thereof, or mixture thereof. In a preferred embodiment, the garlic extract component is garlic juice, a water-based dispersion of pulverized, fresh garlic cloves.

This garlic juice comprises about 50% to 98% by volume pulverized, fresh garlic, preferably about 75% to 85%. The garlic extract component constitutes about 0.5% to about 5% by volume of the composition, preferably about 1% to 3%.

The third ingredient is a hot pepper extract component. The hot pepper extract component is a purified or unpurified: 1) natural extract of or preparation of *Capsicum spp.*, *Solanaceae spp.*, or *Zingiber spp.*, preferably a hot pepper of the *Capsicum spp.* which contains at least about 0.1% by weight capsaicinoids, more preferably a variety of *Capsicum frutescens*, even more preferably commercially available cayenne pepper, or of a derivative thereof, or mixture thereof; or 2) preparation of or composition comprising synthetic capsaicinoids, gingerols, shogaols, or zingerone, or a derivative thereof, or mixture thereof. In a preferred embodiment, the hot pepper extract component is a concentrated, hot pepper sauce: an aged, vinegar-based dispersion of pulverized cayenne peppers. This hot pepper sauce comprises about 5 to 90% by volume pulverized cayenne peppers, preferably about 40 to 80%, more preferably about 50 to 70%. The hot pepper extract component constitutes about 0.5 to 5% by volume of the composition, to provide a desired hotness equivalent to that of at least about 0.05 % by weight capsaicinoid content. Preferably, the hot pepper extract component constitutes about 1 to 3% by volume of the composition.

The fourth ingredient of the composition is a surfactant component. The surfactant component is an ingestible or inedible nonionic, cationic, anionic, zwitterionic, or amphoteric surfactant, surfactant mixture, or surfactant-containing composition, preferably a nonionic surfactant, surfactant mixture, or surfactant-containing composition, more preferably a nonionic alcohol alkoxylate surfactant, surfactant mixture, or surfactant-containing composition. Most preferred among this lattermost class are compositions comprising polyalkyleneoxide-based and polyglycol ether-based surfactants, of which a representative example is Shaklee® Basic-H® liquid, household cleaner concentrate, available from Shaklee Corp., 444 Market St., San Francisco, Calif. Representative examples of ingestible surfactants include dioctyl sodium succinate, sodium phosphate dibasic, and Poloxamers. The surfactant component constitutes at least about 0.5% by volume of the composition, preferably at least about 2%. In a preferred embodiment, the surfactant component is Shaklee® Basic-H®. When the surfactant component is Shaklee® Basic-H®, it preferably constitutes at least about 2.3% by volume of the composition. Although much greater amounts can be used, substantially larger amounts do not appear to provide any further benefit.

In a preferred embodiment of the insect repellant composition, the garlic extract and hot pepper extract components are mixed in a liquid form with the carrier liquid and surfactant components, for ease of preparation of the repellant. The liquid so formed is easily and uniformly applied to the animal or human wearer by spraying it and/or rubbing, wiping, or brushing it onto the surface of the skin, hair, fur, or garments of the wearer, using a cloth, a sponge, or the like. Alternatively, where the surfactant component is an ingestible surfactant, the insect repellant may also be sprayed onto uncovered food such as may be presented on a picnic table or buffet, where it is effective to repel flying insects from lighting upon the food.

Although not wishing to be bound to any particular theory, it is believed that the ingredients of a preferred embodiment of the composition function as follows. The surfactant component, in conjunction with the carrier, serves initially to evenly mix the garlic extract and hot pepper extract components of the repellant, and ensures a uniform dispersion of their dispersible oils and lipophilic constituents. Once the composition is applied, the surfactant component, by decreasing the surface tension of the solution to support wetting of the applied surface, facilitates a wicking action along the hair or fur of the wearer, causing the active, insect-repellant ingredients to penetrate to the skin or hide, where the composition is most effective. When the carrier is a vinegar, because vinegar is also believed to have mild insect repellant activity, it works together with the garlic extract to produce an initial combination-deterrent to flying insects—by means of the continual evaporation of volatile constituents—thereby inhibiting both insect approach and landing. Then, the carrier slowly evaporates, leaving in addition to the surfactant, the garlic and hot pepper extract components. These latter two then exert a two-stage deterrent effect. For a number of hours, the garlic extract component remains effective at preventing flying insects' approach and landing, while it retains its garlicky odor. Over time, as the odor wears off, flying insects begin to light upon the body of the wearer. At that point, the hot pepper extract component exerts its deterrent effect upon the proboscis of the insect as it probes and tastes the surface of the wearer in preparation for a bite. This latter effect lasts for many hours. Finally, when the wearer washes or is washed off, the remaining surfactant cleans the wearer of any residues, at which point a fresh application may be made. When, e.g., Shaklee® Basic-H® is used as the surfactant component, it allows the insect repellant composition to be used effectively in long-term and repeated applications because it is non-toxic and non-irritating to the skin. (Occupational Safety and Health Administration material safety data sheet).

EXAMPLE 1

Composition 1

One gallon of insect repellant of the following composition was made, using a commercially available garlic juice slurry marketed by McCormick & Co., Inc. (comprising a water extract of fresh garlic cloves and citric acid) and a commercially available hot pepper sauce marketed by Van den Bergh Foods, Inc. (comprising a distilled vinegar slurry of aged cayenne peppers and salt):

| | |
|---|---|
| 1. Cider Vinegar | 121 fl. oz. |
| 2. Shaklee ® Basic-H ® | 3 |
| 3. Garlic Juice | 2 |
| 4. Hot Pepper Sauce | 2 |
| Total Insect Repellant | 128 fl. oz. |

Composition 2

The Composition 1 recipe was repeated, omitting the Garlic Juice ingredient.

Composition 3

The Composition 1 recipe was repeated, omitting the Hot Pepper Sauce ingredient.

Experimental Results

The three compositions were applied to 23 horse subjects, during summertime conditions (temperatures ranging from 70° F. to 98° F. with high humidity) in pastureland, swampy lowland, thick brush and woods, and riverbank and lakeside environments which were heavily infested with flying insects including deer flies, green-headed horseflies, blackflies, common houseflies, and mosquitoes. The application method was as follows: subjects were wiped with a repellant-soaked cloth around the head, neck, chest, and shoulders, moving the cloth slowly so that the liquid would soak on, especially around the eyes and ears; then the remainder of the subject was sprayed with the repellant, taking care to spray between the hind legs. Upon the conclusion of the effective insect-repellant period for each subject, each was washed with water, either by spraying with a hose or sponging with water, or in some cases by the action of natural rainfall, at which point a repeat application was made.

Subjects were observed over a period of 9 weeks, in both active, working states in which they sweated profusely, and in resting states. The average periods of effectiveness were recorded in terms of when insects began landing on the subject and when insects again began biting. Results are reported in Table 1.

TABLE 1

Biting-Deterrent Effectiveness of Different Insect Repellant Compositions

|  | Hours of Effectiveness | |
| --- | --- | --- |
|  | Active | Resting |
| 1. Garlic + Pepper | 4–6 | 24–48 |
| 2. Pepper Only | 2.5–4 | 12–16 |
| 3. Garlic Only | 2–3 | 20–30 |

These results show that, among working subjects which sweated profusely, the Composition 1 insect repellant remained effective for 4 to 6 hours, i.e. until the streams of perspiration had diluted the composition to non-effective levels. Among resting subjects, the same repellant remained effective for 24 to 48 hours. In contrast, for both working and resting subjects, the Composition 2 and 3 repellants had 30% to 50% shorter effective lives.

It was also noted that, upon washing each subject, the remaining surfactant acted as a cleaning agent for the hair and skin, leaving the hair coat with a healthy sheen and a soft feel. No adverse effects were noted, even with long-term, repeated, and liberal application of the repellant to the test subjects.

The insect repellant of Composition 1 has also been tested and found effective on humans under conditions substantially similar to those described above. It is also effective on cattle, sheep, goats and other animals.

Variations of the composition and method described herein as the preferred embodiment of the invention may be apparent to those in this field once they have studied the above description. Such variations are considered to be within the scope of the invention, which is intended to be limited only by the scope of the claims and the reasonably equivalent ingredients and methods to those defined therein.

The embodiments of the invention in which an exclusive property or privilege is claimed are defined as follows:

1. An insect repellant comprising about 90–95% by volume of carrier, about 0.5–5% of a garlic extract component, about 0.5–5% of a hot pepper extract component, and at least about 0.5% of a surfactant component.

2. The composition of claim 1 wherein garlic juice is the garlic extract component and hot pepper sauce is the hot pepper extract component.

3. The composition of claim 1 wherein vinegar is the carrier.

4. The composition of claim 1 wherein the surfactant component is a composition comprising alcohol alkoxylate-based, polyalkyleneoxide-based, and polyglycol ether-based surfactants.

5. The composition of claim 1 wherein the surfactant component is a composition comprising at least one surfactant selected from the group consisting of alcohol alkoxylate-based surfactants, polyalkyleneoxide-based surfactants, and polyglycol ether-based surfactants.

6. The composition of claim 1 wherein the surfactant component comprises an ingestible surfactant or surfactants.

7. The composition of claim 1 comprising about 1 to 3% garlic juice, about 1 to 3% hot pepper sauce, at least about 2% of a surfactant component, and the remainder vinegar.

8. The composition of claim 1 comprising at least about 1.5% garlic juice, at least about 1.5% hot pepper sauce, at least about 2% of a surfactant component, and the remainder vinegar.

9. A method of repelling insects from animals or humans comprising blending a carrier and a surfactant component with a garlic extract component and a hot pepper extract component and applying the blend to the hair, fur, skin, or garments, of the wearer.

10. The method of claim 9 wherein said step of blending comprises blending about 90–95% by volume of carrier, about 0.5–5% of a garlic extract component, about 0.5–5% of a hot pepper extract component, and at least about 0.5% of a surfactant component.

11. The method of claim 10 wherein garlic juice is the garlic extract component and hot pepper sauce is the hot pepper extract component.

12. The method of claim 10 wherein vinegar is the carrier.

13. The method of claim 10 wherein the surfactant component is a composition comprising alcohol alkoxylate-based, polyalkyleneoxide-based, and polyglycol ether-based surfactants.

14. The method of claim 10 wherein the surfactant component is a composition comprising at least one surfactant selected from the group consisting of alcohol alkoxylate-based surfactants, polyalkyleneoxide-based surfactants, and polyglycol ether-based surfactants.

15. The method of claim 10 wherein said step of blending comprises blending about 1 to 3% garlic juice, about 1 to 3% hot pepper sauce, at least about 2% of a surfactant component, and the remainder vinegar.

16. The method of claim 10 wherein said step of blending comprises blending at least about 1.5% garlic juice, at least about 1.5% hot pepper sauce, at least about 2% of a surfactant component, and the remainder vinegar.

17. The composition of claim 1 wherein the surfactant component is a composition comprising at least one nonionic surfactant.

* * * * *